US011851291B2

(12) United States Patent
Brinckmann et al.

(10) Patent No.: US 11,851,291 B2
(45) Date of Patent: Dec. 26, 2023

(54) METHOD FOR TRANSPORTING A BLISTER STRIP OF OPHTHALMIC LENSES INTO AN AUTOCLAVE MAGAZINE

(71) Applicant: ALCON INC., Fribourg (CH)

(72) Inventors: Felix Brinckmann, Rossdorf (DE); Nils Schweizer, Bad König (DE); Jens Wolfstädter, Kleinwallstadt (DE)

(73) Assignee: Alcon Inc., Fribourg (CH)

( * ) Notice: Subject to any disclaimer, the term of this patent is extended or adjusted under 35 U.S.C. 154(b) by 499 days.

(21) Appl. No.: 17/173,461

(22) Filed: Feb. 11, 2021

(65) Prior Publication Data

US 2021/0253366 A1  Aug. 19, 2021

Related U.S. Application Data

(60) Provisional application No. 62/975,952, filed on Feb. 13, 2020.

(51) Int. Cl.
*B65G 47/90* (2006.01)
*A45C 11/00* (2006.01)
*A61F 2/16* (2006.01)

(52) U.S. Cl.
CPC .......... *B65G 47/907* (2013.01); *A45C 11/005* (2013.01); *A61F 2/1691* (2013.01)

(58) Field of Classification Search
CPC .............................. B65G 47/907; A61F 2/1691
See application file for complete search history.

(56) References Cited

U.S. PATENT DOCUMENTS

| 4,039,088 | A | 8/1977 | Marynissen | |
|---|---|---|---|---|
| 11,215,844 | B2* | 1/2022 | Biel | .......................... G02C 7/04 |
| 2009/0153168 | A1 | 6/2009 | Beom et al. | |
| 2017/0203865 | A1* | 7/2017 | Kalany | ................... B65B 21/18 |
| 2019/0322470 | A1* | 10/2019 | Haehnel | ............... B65G 47/918 |

FOREIGN PATENT DOCUMENTS

| CN | 1982168 | B | 5/2010 |
|---|---|---|---|
| CN | 108298303 | A | 7/2018 |
| CN | 110386295 | A | 10/2019 |
| DE | 102017111909 | A1 | 12/2018 |

(Continued)

*Primary Examiner* — Saul Rodriguez
*Assistant Examiner* — Willie W Berry, Jr.
(74) *Attorney, Agent, or Firm* — Sheng-Hsin Hu (57) ABSTRACT

A method for transporting a blister strip of ophthalmic lenses: only one single blister strip is provided at a start location and one magazine compartment of two magazine compartments contains n blister strips while the other magazine compartment contains n+1 blister strips, the single buster strip is picked up at the start location by one of the gripper units of a first gripper and is transported into that magazine compartment containing the n blister strips, by moving the first gripper to that magazine compartment containing the n blister strips and releasing the single blister strip from the first gripper into that magazine compartment, or by moving the first gripper to a hand-over station and releasing the single blister strip from the first gripper into the hand-over station, transporting the single blister strip from the hand-over station into that magazine compartment containing the n blister strips using a second gripper.

12 Claims, 4 Drawing Sheets

(56) References Cited

FOREIGN PATENT DOCUMENTS

| | | | |
|---|---|---|---|
| EP | 0686898 | A2 | 12/1995 |
| EP | 1430992 | A1 | 6/2004 |
| EP | 2036817 | A1 | 3/2009 |
| JP | S59190118 | A | 10/1984 |
| TW | 200925087 | A | 6/2009 |

* cited by examiner

METHOD FOR TRANSPORTING A BLISTER STRIP OF OPHTHALMIC LENSES INTO AN AUTOCLAVE MAGAZINE

This application claims the benefit under 35 USC § 119 (e) of U.S. provisional application No. 62/975,952 filed 13 Feb. 2020, herein incorporated by reference in its entirety.

FIELD OF THE INVENTION

The invention relates to a method for transporting a blister strip of ophthalmic lenses, in particular contact lenses or intraocular lenses, into an autoclave magazine.

BACKGROUND OF THE INVENTION

It is well-established to manufacture ophthalmic lenses, and in particular contact lenses such as soft contact lenses, in a fully automated manufacturing process. In this process, the ophthalmic lenses are typically molded by polymerizing and/or crosslinking a starting material (lens-forming material) so as to form the ophthalmic lenses. Depending on the starting material used, it may be required or desired to place the lens in one or more treatment liquids, such as extraction liquids, rinsing liquids and/or coating liquids. Thereafter, the ophthalmic lenses are inspected, and in case the ophthalmic lenses successfully pass inspection the lenses are further processed in a primary packaging unit. In the primary packaging unit, the ophthalmic lenses that have successfully passed the inspection are transferred into primary packaging shells which, by way of example, may be made of a thermoplastic material, for example polypropylene, through injection-molding. The primary packaging shell may comprise a depression configured to contain a storage solution and a said inspected ophthalmic lens. After placing the ophthalmic lenses into the depression of the packaging shell, a storage solution is introduced into the depression, so that the ophthalmic lens is immersed in the storage solution. Thereafter, a cover foil extending over a plurality of primary packaging shells arranged one after the other in a row is then placed onto the packaging shells each containing the ophthalmic lens immersed in the storage solution, and the cover foil is then thermally sealed to the packaging shells thereby forming a sealed blister strip. After printing information on the cover foil, the blister strips passing the final inspection (e.g. lens presence check) have to be autoclaved. For this purpose, the blister strips are transported on carriers to an autoclave loading unit. In this autoclave loading unit, the blister strips are transferred into the compartments of autoclave magazines. In the known processes, blister strips arranged on a carrier reach the autoclave loading unit where the blister strips are picked-up from the carriers and placed into the compartments of the autoclave magazines with the aid of grippers.

The blister strips may be transported to the autoclave loading unit on the carriers pairwise, i.e. two carriers each carrying a blister strip are simultaneously transported to the autoclave loading unit. In the autoclave loading unit, the two blister strips of the pair are transported into the magazine compartments of an autoclave magazine which is equipped with a movable compartment bottom. The first blister strip of the pair is placed into the first autoclave compartment and the second blister strip of the pair is placed into the second autoclave compartment. In the first and second autoclave compartments, the blister strips are accommodated in a manner stacked one above the other. A filled autoclave magazine accommodating in each magazine compartment a plurality of stacked blister strips is then placed into an autoclave, so that the blister strips accommodated in the magazine compartments are autoclaved before the autoclaved blister strips are ready for distribution. However, it may turn out that after the lens presence check in the final inspection, one of the two blister strips on the carrier is to be discarded due to a lens missing in one or more depressions of the primary packaging shells of that blister strip. Also, at certain times during production, one blister strip is arbitrarily selected for being removed from the normal material flow in order to manually inspect the lenses of that selected blister strip to confirm that the lens presence check and the automatic lens inspection work properly (quality sampling). In each of the afore-mentioned scenarios discarding blister strips in a step preceding the transfer into the autoclave magazine results in an empty carrier reaching the autoclave loading unit, so that instead of a pair of blister strips only one blister strip actually reaches the autoclave loading unit on the pair of carriers. This single blister strip is then picked up and placed into the first or the second magazine compartment of the autoclave magazine (depending on whether the single blister strip reaches the autoclave loading unit at the first pick-up position or at the second pick-up position of the autoclave loading unit), and thereafter the autoclave magazine bottom is lowered by one step for the introduction of the next blister strip(s).

Especially when blister strips are discarded due to an ophthalmic lens missing in one or more depressions of a blister strip, the origin of this missing ophthalmic lens oftentimes has a technical reason. It may therefore happen that a single blister strip repeatedly reaches the autoclave loading unit at the same pick-up position and is repeatedly transported into the same magazine compartment assigned to that pick-up position, which in turn may lead to a significant higher number of stacked blister strips being placed in one of the two magazine compartments of the autoclave magazines. Such significant deviation in the number of stacked blister strips in the autoclave magazine may lead to various inconveniences. For example, when a blister strip is released into a magazine compartment having significantly less stacked blister strips than the other magazine compartment, the height from which the blister strip is released from the gripper into the magazine compartment may be too high such that the blister strip released from the gripper may rotate or tilt before reaching the uppermost blister strip in the compartment. The blister strip may then not be arranged flat on the other blister strips and hence one or more ophthalmic lenses contained in the packaging shells of such blister strip may get deformed during the autoclaving process as the ophthalmic lens does not properly rest in the center of the depression of the packaging shell (immersed in the storage solution). This may have an unfavorable impact on the quality of the ophthalmic lenses.

Therefore, it would be desirable to provide a method for transporting ophthalmic lenses into the autoclave magazines overcoming the afore-mentioned disadvantages of the prior art.

SUMMARY

These and further objects are met by the method for transporting a blister strip of ophthalmic lenses according to the invention. Further advantageous aspects of the method according to the invention and/or preferred embodiments are subject of the respective dependent claims.

As used in the specification including the appended claims, the singular forms "a", "an", and "the" include the plural, unless the context explicitly dictates otherwise. When using the term "about" with reference to a particular numerical value or a range of values, this is to be understood in the sense that the particular numerical value referred to in connection with the "about" is included and explicitly disclosed, unless the context clearly dictates otherwise. For example, if a range of "about" numerical value a to "about" numerical value b is disclosed, this is to be understood to include and explicitly disclose a range of numerical value a to numerical value b. Also, whenever features are combined with the term "or", the term "or" is to be understood to also include "and" unless it is evident from the specification that the term "or" must be understood as being exclusive.

In particular, the present invention suggests a method for transporting a blister strip of ophthalmic lenses, in particular contact lenses or intraocular lenses, into an autoclave magazine, the method comprising the steps of:

providing a first gripper for gripping blister strips, the first gripper comprising two gripper units, each of the two gripper units being configured to separately grip one individual blister strip, providing an autoclave magazine comprising two magazine compartments, each of the two magazine compartments being configured to contain individual blister strips in a manner stacked one above the other, at a start location providing at least one blister strip, picking up the at least one blister strip provided at the start location using the first gripper, moving the first gripper together with the at least one blister strip picked up at the start location to a destination location, and releasing the at least one blister strip from the first gripper at the destination location, wherein n is a positive integer including zero and indicates the number of blister strips actually contained in at least one of the two magazine compartments of the autoclave magazine, wherein either the two magazine compartments both contain n blister strips or one magazine compartment contains n blister strips while the other magazine compartment contains n+1 blister strips, wherein the at least one blister strip is picked up at the start location by the gripper units of the first gripper and is transported to the magazine compartments, either directly by moving the first gripper to the magazine compartments as destination location, or indirectly by providing a hand-over station and a second gripper for gripping blister strips and moving the first gripper to the hand-over station as the destination location and releasing the at least one blister strip from the first gripper into the hand-over station and by subsequently transporting the at least one blister strip from the hand-over station to the magazine compartments using the second gripper, and wherein in case only one single blister strip is provided at the start location and one magazine compartment of the two magazine compartments contains n blister strips while the other magazine compartment contains n+1 blister strips, the single blister strip is picked up at the start location by one of the gripper units of the first gripper and is transported into that magazine compartment containing the n blister strips, either directly by moving the first gripper to that magazine compartment containing the n blister strips and releasing the single blister strip from the first gripper into that magazine compartment, or indirectly by moving the first gripper to the hand-over station and releasing the single blister strip from the first gripper into the hand-over station and subsequently transporting the single blister strip from the hand-over station into that magazine compartment containing the n blister strips using the second gripper.

According to one aspect of the method according to the invention, each gripper unit of the two gripper units of the first gripper is either fixedly assigned to a respective magazine compartment position corresponding to the location where one magazine compartment of the two magazine compartments of the autoclave magazine is arranged, with one gripper unit of the first gripper being fixedly assigned to the magazine compartment position of one of the two magazine compartments and the other gripper unit of the first gripper being fixedly assigned to the magazine compartment position of the other of the two magazine compartments, or each gripper unit of the two gripper units of the first gripper is fixedly assigned to a respective hand-over position out of two hand-over positions in the hand-over station, with one hand-over position of the two hand-over positions being fixedly assigned to the magazine compartment position of one of the two magazine compartments and the other hand-over position of the two hand-over positions being fixedly assigned to the magazine compartment position of the other of the two magazine compartments, and in case only one single blister strip is provided at the start location and one magazine compartment of the two magazine compartments contains n blister strips while the other magazine compartment contains n+1 blister strips, the single blister strip is picked up at the start location by that gripper unit which is fixedly assigned to the magazine compartment position corresponding to the location of the magazine compartment containing the n blister strips or to the hand-over position which is fixedly assigned to the magazine compartment position of the magazine compartment containing the n blister strips, and is transported into that magazine compartment containing the n blister strips, either directly by moving the first gripper to the magazine compartment position corresponding to the location of the magazine compartment containing the n blister strips and releasing the single blister strip from the first gripper into that magazine compartment, or indirectly by moving the first gripper to the hand-over position fixedly assigned to the magazine compartment position of the magazine compartment containing the n blister strips and releasing the single blister strip from the first gripper into the hand-over station at that hand-over position and by subsequently transporting the single blister strip from that hand-over position in the hand-over station into the magazine compartment containing the n blister strips using the second gripper.

According to a further aspect of the method according to the invention, the start location has two pick-up positions where blister strips can be provided, and each gripper unit of the two gripper units of the first gripper is fixedly assigned to one of the two pick-up positions, with one gripper unit being fixedly assigned to one pick-up position of the two pick-up positions and the other gripper unit being fixedly assigned to the other pick-up position of the two pick-up positions, and in case only one single blister strip is provided at the start location at one of the two pick-up positions and one magazine compartment of the two magazine compartments contains n blister strips while the other magazine compartment contains n+1 blister strips, the single blister strip is picked up at the said one of the two pick-up positions by the gripper unit fixedly assigned to the said one of the two pick-up positions and is transported into the magazine compartment containing the n blister strips either directly by moving the first gripper to the magazine compartment containing the n blister strips as the destination location and releasing the single blister strip from the first gripper into that magazine compartment, or indirectly by moving the first gripper to the hand-over station and releasing the single blister strip from the first gripper into the hand-over station at a hand-over position fixedly assigned to the magazine compartment containing the n blister strips and by subsequently transporting the single blister strip from the hand-over position into that magazine compartment using the second gripper.

According to still a further aspect of the method according to the invention, in case only one single blister strip is provided at the start location and both of the two magazine compartments contain n blister strips,
the single blister strip is picked up at the start location by one of the two gripper units of the first gripper, and is transported into one of the two magazine compartments, either directly by moving the first gripper to the magazine compartments and releasing the single blister strip from the first gripper into one of the two magazine compartments, or indirectly by moving the first gripper to the hand-over station and releasing the single blister strip from the first gripper into the hand-over station and by subsequently transporting the single blister strip from the hand-over station into one of the two magazine compartments using the second gripper.

According to yet a further aspect of the method according to the invention, in case two blister strips are provided at the start location and one magazine compartment of the two magazine compartments contains n blister strips while the other magazine compartment contains n+1 blister strips, the two blister strips are both picked up at the start location by the two gripper units of the first gripper, one blister strip by one gripper unit and the other blister strip by the other gripper unit of the two gripper units, and are transported into the two magazine compartments, either directly by moving the first gripper to the two magazine compartments and releasing the two blister strips from the gripper units of the first gripper into the two magazine compartments, one blister strip into each magazine compartment, or indirectly by moving the first gripper to the hand-over station and releasing each of the two blister strips from the first gripper into the hand-over station, one blister strip into one hand-over position of two hand-over positions in the hand-over station and the other blister strip into the other hand-over position of the two hand-over positions, and by subsequently transporting the two blister strips from the two hand-over positions in the hand-over station into the two magazine compartments, one blister into each of the two magazine compartments, using the second gripper.

Still in accordance with a further aspect of the method according to the invention, in case two blister strips are provided at the start location and both of the two magazine compartments contain n blister strips, the two blister strips are both picked up at the start location by the two gripper units of the first gripper, one blister strip by one gripper unit and the other blister strip by the other gripper unit of the two gripper units, and are transported into the two magazine compartments, either directly by moving the first gripper to the two magazine compartments and releasing the two blister strips from the gripper units of the first gripper into the two magazine compartments, one blister strip into each magazine compartment, or indirectly by moving the first gripper to the hand-over station and releasing the two blister strips from the first gripper into the hand-over station, one blister strip into one hand-over position of two hand-over positions in the hand-over station and the other blister strip into the other hand-over position of the two hand-over positions, and by subsequently transporting the two blister strips from the two hand-over positions in the hand-over station into the two magazine compartments, one blister strip into each of the two magazine compartments, using the second gripper.

In accordance with a further aspect of the method according to the invention, providing an autoclave magazine comprises providing an autoclave magazine having a packing axis, the two magazine compartments, a loading opening and a common compartment bottom arranged normal to and movable along the packing axis, and,
prior to releasing blister strips into the two magazine compartments of the autoclave magazine, the compartment bottom is moved to an uppermost position at the loading opening, and only then the blister strips are transported to and released into the magazine compartments,
and each time either two blister strips are released into the two magazine compartments, one blister strip into one of the two magazine compartments and the other blister strip into the other magazine compartment of the two magazine compartments or
each time only one single blister strip is released into one of the magazine compartments and thereafter both of the two magazine compartments contain the same number m of blister strips, with m being a positive integer excluding zero and being less than a maximum number of blister strips to be accommodated in each of the magazine compartments, the compartment bottom is moved away from the loading opening along the packing axis by one step to allow additional blister strip(s) to be released into the magazine compartments.

According to a further aspect of the method according to the invention, the method comprises providing an autoclave magazine mask arranged at the loading opening of the autoclave magazine, the autoclave magazine mask being capable of being opened and closed and,
after having released into the two magazine compartments a predefined number of blister strips which is less than the maximum number of blister strips to be accommodated in the two magazine compartments, the autoclave magazine mask is closed, the compartment bottom is then moved towards the autoclave magazine mask to compress the stacked blister strips contained in the magazine compartments and the autoclave magazine mask is then opened again to allow additional blister strips to be released into the magazine compartments of the autoclave magazine,
wherein the closed the autoclave magazine mask overlaps at least a portion of the loading opening for allowing a respective uppermost blister strip of the stacked blister strips to abut against the autoclave magazine mask as the compartment bottom is moved towards the autoclave magazine mask.

According to still a further aspect of the method according to the invention, after the compartment bottom has been moved towards the autoclave magazine mask to compress the stacked blister strips contained in the magazine compartments, the compartment bottom is moved away from the autoclave magazine mask again, and the autoclave magazine mask is opened to allow additional blister strips to be released into the magazine compartments of the autoclave magazine.

According to yet a further aspect of the method according to the invention, providing an autoclave magazine comprises providing an autoclave magazine comprising a separation web extending along the packing axis, the separation web separating the interior of the magazine into the two magazine compartments, and the compartment bottom comprising a slot for receiving the separation web, and moving the compartment bottom along the packing axis comprises moving the slot of the compartment bottom along the separation web.

Still in accordance with a further aspect of the method according to the invention, transporting the blister strips using the first gripper or the second gripper comprises the steps of
  providing the first gripper or the second gripper with gripping heads, the gripping heads each having a bearing surface and at least one opening in the respective bearing surface,
  picking the blister strip(s) up with the first gripper or the second gripper by positioning the gripping heads of the first gripper or the second gripper above the blister strip(s), by placing the respective bearing surfaces closely adjacent to the blister strip, and by applying underpressure through the opening in the respective bearing surface so as to cause the blister strip(s) to adhere to the respective bearing surface,
  moving the first gripper or the second gripper together with the blister strip(s) adhered to the bearing surface to a desired location, and
  releasing the blister strip from the bearing surface at the desired location by applying overpressure through the opening in the respective bearing surface.

In accordance with yet another aspect of the method according to the invention, the method comprises providing a first gripper or second gripper further having a separate detection opening in the respective bearing surface, and applying a separate underpressure through the detection opening in the respective bearing surface in order to detect whether or not a blister strip is adhered to the respective bearing surface.

The afore-mentioned aspects of the method according to the invention have a number of advantages.

The method may be easily implemented in-line in a fully automated or semi-automated process for manufacturing ophthalmic lenses.

The method according to the invention results in the autoclave magazine being loaded such that either the two magazine compartments both contain the same number n of blister strips, or one magazine compartment contains a number n of blister strips while the other magazine compartment contains one more (n+1) blister strips. Accordingly, the method minimizes the dropping height upon releasing the blister strip from the gripper into the magazine compartment onto the uppermost blister strip already stacked in the magazine compartment (or onto the magazine bottom, respectively, in case no blister strip has been released into the magazine compartment). Thus, the risk that the released blister strip rotates or tilts is eliminated or at least the risk greatly reduced. Hence, the ophthalmic lens contained in the blister strip remains located in the center of the depression of the primary packaging shell and will not be deformed during the autoclaving process due to a rotated or tilted blister strip. This has an impact on the quality of the finally distributed ophthalmic lenses. Thus, not only the autoclaving process is more uniform but also the space provided in the autoclave magazines is used as efficiently as possible while still complying with the requirement that only lenses from one and the same lot are placed into the same magazine.

The method allows a higher number of blister strips to be introduced into the autoclave magazine and to be subsequently autoclaved in one step, as the space available for the blister strips in the autoclave magazine is efficiently used, as the maximum difference (if any) of the numbers of blister strips contained in the two compartments of the autoclave magazine is one.

The number n and n+1 of blister strips contained in the magazine compartments may either be determined by sensors arranged at the location of the autoclave magazine, or by counting the number of blister strips actually released/introduced into each magazine compartment during loading of the autoclave magazine, depending on the presence of one single blister strip or two blister strips (for example determined with the aid of sensors) at the start location and the transport path of the blister strip(s) into the magazine compartment(s).

Additionally, the method according to the invention allows for a balanced load of the stacked blister strips in the two compartments autoclave magazine and therefore an even weight distribution on the compartment bottom. Hence, the method avoids that the compartment bottom of the autoclave magazine may tilt due to an unbalanced load of stacked blister strips. The compartment bottom may otherwise tilt due to an unbalanced load of the stacked blister strips in case one magazine compartment contains significantly more blister strips than the other magazine compartment due to a significant higher weight resting on one portion of the compartment bottom. The compartment bottom may also tilt due to jamming of the compartment bottom, for example in case of a distorted compartment bottom. In this case, blister strips already contained in the magazine compartments may fall further down into the autoclave magazine below the compartment bottom or into the autoclave loading area (ground) in an uncontrollable manner. This may cause an error alarm and the automated production line or at least the loading unit may have to be stopped for operator intervention. In such a fully automated production line, operator intervention leads to downtime, as the autoclave loading area has to be inspected then and the blister strips fallen down need to be removed before operation of the loading unit may be resumed.

In combination with the step of compressing the blister strips (the cover foil might be slightly domed), the space needed for the autoclaving of the blister strips may be optimally used, i.e. a higher number of blister strips may be introduced into the autoclave magazines and subsequently autoclaved in one step. The method allows for a particularly efficient compression of the blister strips since either both magazine compartments contain the same number of blister strips (n) or there is a difference in the number of blister strips contained in the magazine compartments of one blister strip only (n+1), hence the same or substantially the same height of stacked blister strips on both magazine compartments. Besides, domed cover foils of the blister strips may result in distortion of the packaging shell during the autoclaving process which may in turn result in deformation of the ophthalmic lens contained in the packaging shell. Again, not only is the autoclaving process more uniform but also the space provided in the autoclave magazines is used as efficiently as possible while still complying with the requirement that only lenses from one and the same lot are placed into the same magazine.

The method is particularly advantageous in connection with the autoclave magazine mask. Once the autoclave magazine mask has been closed, the compartment bottom is lifted and the uppermost blister strip of the blister strips stacked between the compartment bottom and the closed autoclave magazine mask is pressed against the autoclave magazine mask and the blister strips of the stack are compressed. Once the stacked blister strips have been compressed, the compartment bottom is lowered again to simplify opening the autoclave magazine mask again and avoid that the stack of compressed blister strips, which may slightly expand once the force applied is removed, moves up too far and may provoke the risk that the next blister strip is dropped onto the uppermost blister strip of the stack at a location above the loading opening. The autoclave mask may only cover a portion of the loading opening and may be formed by two mask portions. The autoclave magazine mask may then also be used as guide for the grippers during introduction and release of the blister strips into the magazine compartments.

Compression of the blister strips may be performed several times during loading the autoclave magazine, in particular after the introduction of a predetermined number (for example 20) of blister strips (into each magazine compartment), and may be performed again after another predetermined number of blister strips, which may be identical or different to the first number of introduced blister strips, has been introduced into each magazine compartment.

Cycle times of the production line and of the autoclave loading unit may be different due to the long transportation paths in the process of autoclave magazine loading. The use of two gripper units for the first gripper according to one aspect of the method of the present invention additionally allows an easy adaptation of the cycle time between the production line and the autoclave loading, which may again result in a more efficient and faster production of the ophthalmic lenses and still reliable loading of the autoclave magazines. The use of a hand-over station may additionally allow for a compensation of differences in the cycle times of the production line to that of the autoclave magazine loading.

In case a hand-over station and a second gripper are provided, the second gripper may comprise two gripper units, each of the two gripper units being configured to separately grip one individual blister strip, and the hand-over station may have two hand-over positions, each hand-over position being assigned to the location where one magazine compartment of the two magazine compartments is arranged. One gripper unit of the second gripper may then be assigned to the autoclave magazine compartment position of one of the two autoclave magazine compartments while the other gripper unit of the second gripper may be assigned to the autoclave magazine compartment position of the other of the two autoclave magazine compartments. The second gripper may transport the at least one blister strip from said at least one of the two hand-over positions in the hand-over station to the assigned magazine compartment by positioning the second gripper at the hand-over position, picking the at least one blister strip up at the hand-over position, moving the second gripper together with the at least one at least one blister strip to the autoclave magazine, and releasing the at least one blister strip from the second gripper into the assigned magazine compartment.

The compartment bottom may be embodied as a single plate that forms a common bottom for both magazine compartments. The compartment bottom may be moved linearly along the packing axis of the autoclave magazine with the aid of at least one rod. The compartment bottom may rest on one end of the rod but may not be fixedly attached to the rod. The rod may be attached to an actuator that transfers the linear movement to the compartment bottom via the rod. In particular, the compartment bottom may be moved along the packing axis with the aid of one single rod which is arranged such that the compartment bottom is centrally supported by the rod. In this case, the method according to the invention reduces the risk of tilting of the compartment bottom since the number of blister strips is identical in both magazine compartments or differs by only one blister strip, thereby ensuring a balanced distribution of the weight of the blister strips on the compartment bottom. The method therefore reduces the risk of blister strips falling down into the autoclave magazine below the compartment bottom or on the floor of the autoclave loading area in an uncontrollable manner.

When the autoclave magazine comprises a separation web extending along the packing axis, and the compartment bottom comprises a slot for receiving the separation web, the compartment bottom may be moved along the packing axis by moving the slot of the compartment bottom along the separation web. The slot of the compartment bottom may be positioned in the middle, in particular at the center of the compartment bottom such as to divide the compartment bottom into two bottom areas having (substantially) the same loading surface and the separation web may be positioned such that the slot of the compartment bottom is moved along the separation web when moved along the packing axis.

The separation web may also be positioned along the packing axis in the middle of one wall (e.g. the rear wall) of the autoclave magazine such as to divide the (rear) wall into two areas of (substantially) same surface. In this case, the separation web extends from the (rear) wall of the autoclave magazine into the interior of the autoclave magazine and the compartment bottom has a slot for receiving the separation web and for allowing the compartment bottom to be moved along the packing axis by moving the indentation along the separation web. The separation web may, for example, be soldered or welded to the autoclave magazine wall.

The use of a separation web has the advantage of spatially separating the interior of the autoclave magazine into two magazine compartments.

Additionally, and in combination with the rod for moving the compartment bottom, the web avoids tilting of the compartment bottom of the compartment bottom to an extent (i.e. to an angle beyond the operational angle) that blister strips stacked on the compartment bottom may fall off the compartment bottom and into the interior of the autoclave magazine below the compartment bottom. The operational angle of the compartment bottom is the angle formed between the plane of the compartment bottom and the separation web and may deviate slightly from 90° (degrees), in particular may deviate from 90° by an angle of up to ±20°, very particularly by an angle of up to ±10°. In case the compartment bottom starts tilting, tilting beyond the boundaries of the range for the operational angle will be prevented through interaction (wedging) of the walls of the compartment bottom bounding the slot and the separation web. To achieve this, the clearance between the separation web and the slot is selected such as to allow for free movement of the compartment bottom along the packing axis as long as the compartment bottom is within the boundaries of the range for the operational angle (n blister strips in both magazine compartments or n blister strips in one compartment magazine and n+1 blister strips in the other magazine compartment leading to a small angle deviation from the normal to the separation web), but prevents tilting of the compartment bottom beyond the range for the operational angle.

In case of tilting of the compartment bottom beyond the range of the operational angle, the rod will be prevented from moving the compartment bottom upwards (for example at the beginning of the loading process of the autoclave magazine when the compartment bottom is lifted to its uppermost position or during the process of compressing the blister strips). In this event, an alarm may be generated requiring operator intervention. Since the blister strips are prevented from dropping further down into the autoclave magazine or on the floor of the autoclave loading area (due to prevention of tilting of the compartment bottom beyond the boundaries of the operational angle), a simple operator intervention at the autoclave magazine, or a fast exchange of the autoclave magazine is sufficient to remedy the failure.

During loading of the autoclave magazine, moving the compartment bottom away from the loading opening along the packing axis may start after several blister strips have already been introduced into the magazine compartments. In this case, until both of the two magazine compartments contain the same number k of blister strips, or one magazine compartment contains k blister strips and the other magazine compartment contains k+1 blister strips, with k being a positive integer and (at least) as large as the number of blister strips to be introduced before starting moving away the compartment bottom step by step, the compartment bottom is not moved. Only once k is larger than the aforementioned number, the step-by-step movement of the compartment bottom is started. For example, k may be at least as large as 4. Once this number of blister strips has been introduced into the compartments and either two blister strips are released into the two magazine compartments or only one single blister strip is released into one of the magazine compartments and both magazine compartments then contain the same number k or k+1 of blister strips, the compartment bottom is moved away from the loading opening. In particular, the compartment bottom may be moved away from the loading opening by a distance corresponding to at least the height of one blister strip, or by a distance corresponding to the height necessary for the safe introduction of one blister strip.

In case the gripper for transporting a blister strip of ophthalmic lenses comprises a gripper head having a bearing surface, the bearing surface may have at least one opening through which underpressure can be applied (in order to suck the blister strip against the bearing surface) and through which overpressure can be applied (in order to release the blister strip from the bearing surface). The gripper may further comprise a separate detection opening (different from the opening through which underpressure or overpressure can be applied) in the bearing surface through which separate underpressure can be applied. The separate underpressure which is applicable through the detection opening helps to clearly indicate whether or not a blister strip adheres to the bearing surface. In this connection the term "separate underpressure" means that the separate underpressure applied through the detection opening is neither influenced by the underpressure for sucking the blister strip against the bearing surface nor is it influenced by the overpressure for releasing the blister strip from the bearing surface. In case a separate underpressure of a predetermined value is applied through the detection opening (e.g. with the aid of a vacuum source) and a blister strip adheres to the bearing surface of the gripper head then this applied separate underpressure is maintained since the blister strip adhering to the bearing surface closes the detection opening. In case no blister strip adheres to the bearing surface, air is sucked in from the environment through the detection opening and this leads to a very significant reduction or collapse of the underpressure applied (which will be immediately recognized at the vacuum source providing the underpressure). Thus, reliable detection of whether or not a blister strip adheres to the bearing surface is possible. And while it is possible to detect whether or not a blister strip has been successfully sucked against the bearing surface, it is also possible to detect whether or not a blister strip has been successfully released from the bearing surface.

It goes without saying, that in fully automated production lines for the mass production of ophthalmic lenses, in particular soft contact lenses or intraocular lenses, a plurality of grippers and hand-over positions on the hand-over station may be arranged in side by side configuration, for example, a side-by-side configuration of eight first grippers and corresponding hand-over positions and second grippers if applicable, in order to transport a greater number of blister strips in parallel into the autoclave magazines. For the indirect transportation of the blister strips via a hand-over station, a corresponding number of second grippers, for example, a side-by-side configuration of eight second grippers, and a corresponding number of hand-over positions in the hand-over station (i.e. a plurality of pairs of hand-over positions) for placing the blister strips transported from the first grippers and released into the hand-over positions may be provided. For an effective production, the plurality of grippers or at least a number of the plurality of grippers, can be moved to the assigned positions in parallel.

It is to be noted, that each individual feature described herein as well as all combinations of two or more of such features are possible as long as such features are not mutually exclusive or are otherwise technically incompatible.

The afore-mentioned embodiments are practical embodiments of transporting a blister strip of ophthalmic lenses into an autoclave magazine.

Further embodiments and advantages become apparent from the following description of detailed embodiments of the method and system according to the invention with the aid of the drawings.

DETAILED DESCRIPTION

The following description of exemplary embodiments of the invention is for illustrative purposes only and is not intended to limit the scope of the invention.

Figure 1:
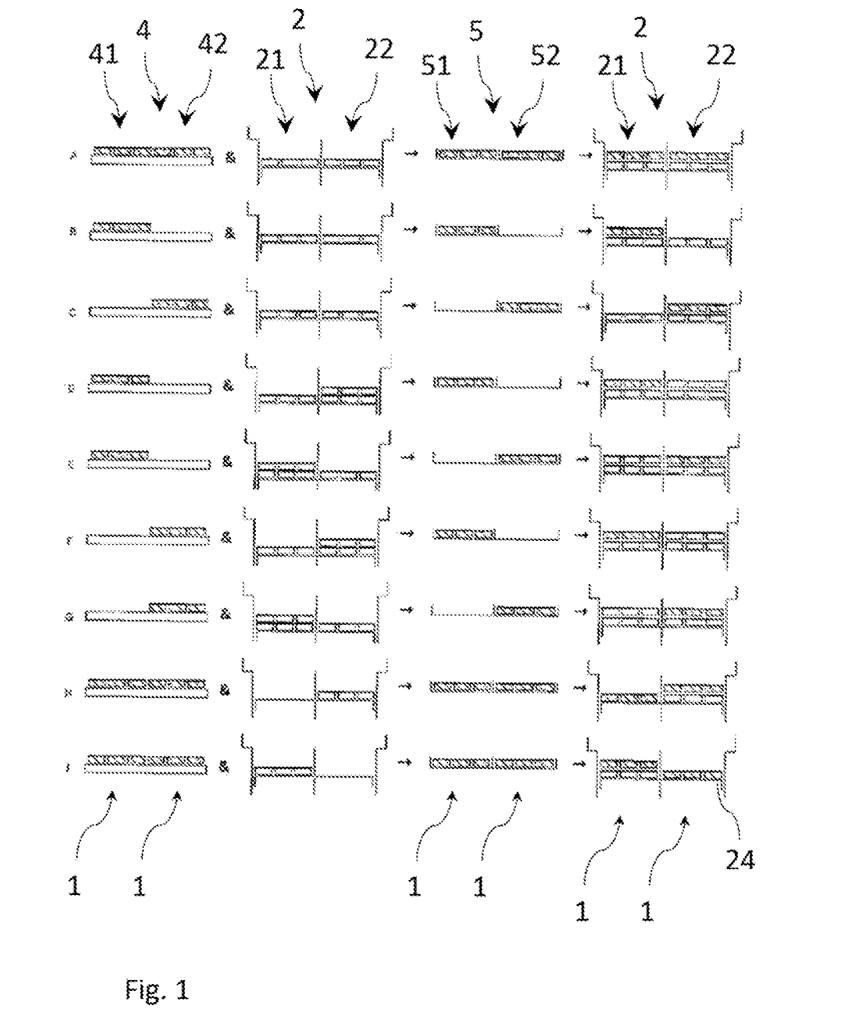
FIG. 1 shows schematically various scenarios of an exemplary embodiment of the method according to the invention.

FIG. 1 shows schematically various scenarios of an embodiment of the method for transporting a blister strip 1 of ophthalmic lenses using a hand-over station 5 (represented by a tray with two compartments) with two hand-over positions 51 and 52 (corresponding to the compartments of the tray). At a start location 4, one or two blister strips 1 may be provided at one of two pick-up positions 41 or 42 or at both pick-up positions 41 and 42 (e.g. on a respective carrier). An autoclave magazine 2 has two compartments 21 and 22 which may either both contain the same number of blister strips n, or one magazine compartment of the two magazine compartments 21, 22 contains n blister strips while the other magazine compartment of the two magazine compartments 21, 22 contains n+1 blister strips. The hatched blister strips 1 are the blister strips which are to be transported or which have been transported, whereas the non-hatched blister strips are blister strips which were already present in the magazine compartments.

Generally, the autoclave magazines 2 are filled as efficiently as possible, i.e. in manner such that there is no free space in any of the first magazine compartment 21 and second magazine compartment 22, except for the free space of one blister strip in the event there are n blister strips contained in one of the two magazine compartments whereas n+1 blister strips are contained in the other magazine compartment, in order to achieve a uniform autoclaving process.

When two blister strips 1 are provided on the carrier at the start location 4, the first blister strip is ultimately placed into the first compartment 21 of the autoclave magazine 2 and the second blister strip is placed into the second compartment 22 of the autoclave magazine 2, whereupon the compartment bottom 24 of the autoclave magazine 2 is moved downwardly to the next level by one step (i.e. to one level below).

Hence, when two blister strips 1 are provided at the pick-up positions 41, 42 at the start location 4 on the carrier and the magazine compartments 21, 22 of the autoclave magazine 2 contain the same number of blister strips n (scenario A in FIG. 1), both blister strips 1 are picked up at the start location and are placed into the hand-over station 5 at the first hand-over position 51 and the second hand-over position 52, respectively. Thereafter, both blister strips 1 are picked up from the first and second hand-over positions 51 and 52 in the hand-over station 5 and placed into the magazine compartments 21, 22, one blister strip into the first magazine compartment 21 and the other blister strip into the second magazine compartment 22. Thereafter, the filling level in both magazine compartments 21, 22 is again the same for both magazine compartments 21, 22. Alternatively, the two blister strips may be picked up at the start location 4 and may be directly placed into the magazine compartments 21, 22 of the autoclave magazine (i.e. skipping the intermediate placement of the blister strips into the hand-over station 5; skipping of the hand-over station 5 is also possible for the scenarios described below).

For various reasons, however, it may occur that only one blister strip is actually provided at the start location 4, and hence only one of the two pick-up positions 41, 42 is occupied with a blister strip, whereas the other of the two pick-up positions is empty.

When only one single blister strip 1 is provided at the first pick-up position 41 at the start location 4 on the carrier and the magazine compartments 21, 22 of the corresponding autoclave magazine 2 contain the same number n of blister strips, the single blister strip 1 is picked and placed, for example, into the hand-over station 5 at the first hand-over position 51. Thereafter, the blister strip 1 is picked up from the first hand-over position 51 and is placed into the first magazine compartment 21, whereupon the filling level of the first magazine compartment 21 is at n+1 blister strips, i.e. one level above the filling level of the second magazine compartment 22 which is at n blister strips (scenario B of FIG. 1). The same applies analogously to the scenario where one single blister strip 1 is provided at the start location 4 at the second pick-up position 42. The blister strip 1 is picked up and placed, for example, into the hand-over station 5 at the second hand-over position 52. Thereafter, the blister strip 1 is picked up from the second hand-over position 52 and is placed into the second magazine compartment 22, whereupon the filling level of the first magazine compartment 21 is at n blister strips, i.e. at one level below the filling level of the second magazine compartment 22 which is at n+1 blister strips (scenario C of FIG. 1).

When the filling level is at n blister strips in the first magazine compartment 21 and at n+1 blister strips in the second magazine compartment 22, during the transportation of the blister strips a blister strip 1 is picked up at the start location 4, placed into the hand-over station 5, and then picked up from the hand-over station 5 and placed into the first magazine compartment 21. This may be performed either concurrently with picking up a further blister strip 1 at the start location 4, placing the further blister strip 1 into the hand-over station 5, and picking up the further blister strip 1 at the hand-over station 5 and placing it into the second magazine compartment 22 (i.e. in the event of two blister strips 1 being provided at the start location 4 corresponding to scenario H of FIG. 1). Or it may be performed without concurrently picking up a further blister strip 1 at the start location 4, without placing the further blister strip 1 into the hand-over station 5, and without picking up the further blister strip 1 at the hand-over station 5 and placing it into the second compartment 22 (i.e. in the event of only one single blister strip 1 being provided at the start location 4 corresponding to the scenarios D and F of FIG. 1). As can be seen in FIG. 1, in both scenarios D and F in which only a single blister strip 1 is provided at the start location 4, the single blister strip 1 is picked up at the start location 4 and is placed into the hand-over station 5 at the first hand-over position 51, regardless at which of the two pick-up positions 41 and 42 the single blister strip 1 is actually provided at the start location 4.

The same applies analogously when the filling level is at n+1 blister strips in the first magazine compartment 21 and is at n blister strips in the second magazine compartment 22, in which case the blister strip 1 is picked up at the start location 4, placed into the hand-over station 5, and then picked up at the hand-over station 5 and placed into the second magazine compartment 22. Again, this may be performed either concurrently with picking up a further blister strip 1 at the start location 4, placing the further blister strip 1 into the hand-over station 5, and picking up the further blister strip 1 at the hand-over station 5 and placing it into the first magazine compartment 21 (i.e. in the event of two blister strips being provided at the start location 4 corresponding to the scenario J of FIG. 1). Or it may be performed without picking up a further blister strip 1 at the start location 4, without placing the further blister strip 1 into the hand-over station 5, and without picking up the further blister strip 1 at the hand-over station 5 and placing it into the first magazine compartment 21 (i.e. in the event of only one single blister strip 1 being provided at the start location 4 corresponding to the scenarios E and G of FIG. 1). As can be seen in FIG. 1, in both scenarios E and G in which only a single blister strip 1 is provided at the start location 4, the single blister strip 1 is picked up at the start location 4 and is placed into the hand-over station 5 at the second hand-over position 52, regardless at which of the two pick-up positions 41 and 42 the single blister strip 1 is actually provided at the start location 4.

In each of the scenarios D, E, F and G, after the blister strip has been placed into the autoclave magazine 2, the filling level of the autoclave magazine 2 is the same in both magazine compartments 21, 22, so that during the next transportation of blister strips either one blister strip may be ultimately placed (via the hand-over station 5 as described above) into the first magazine compartment 21 or the second magazine compartment 22 in case only one single blister strip is provided at the start location 4, or in case two blister strips are provided at the start location 4 both blister strips 1 ultimately may be concurrently placed (via the hand-over station 5 as described above) into the first magazine compartment 21 and the second magazine compartment 22, one blister strip into each magazine compartment 21, 22.

In case two blister strips 1 are provided at the pick-up positions 41, 42 at the start location 4 (on the carrier) and the first magazine compartment 21 contains n blister strips while the second magazine compartment 22 contains n+1 blister strips, both blister strips 1 are picked up at the start location 4 and placed into the hand-over station 5. Thereafter, both blister strips 1 are picked up at the hand-over station 5 and placed into the magazine compartments 21, 22, one blister strip 1 into the first magazine compartment 21 and the other blister strip 1 into the second magazine compartment 22. Thereafter, the filling level of the first magazine compartment 21 is again one level below the filling level of the second magazine compartment 22 (scenario H). The same applies analogously in case the first magazine compartment 21 contains n+1 blister strips while the second magazine compartment 22 contains n blister strips: Both blister strips 1 are picked up at the start location 4 and placed into the hand-over station 5. Thereafter, both blister strips 1 are picked up at the hand-over station 5 and are placed into the magazine compartments 21, 22, one blister strip into the first magazine compartment 21 and the other blister strip into the second magazine compartment 22. Thereafter the filling level of the first magazine compartment 21 is again one level above the filling level of the second magazine compartment 22 (scenario J).

Figure 2:
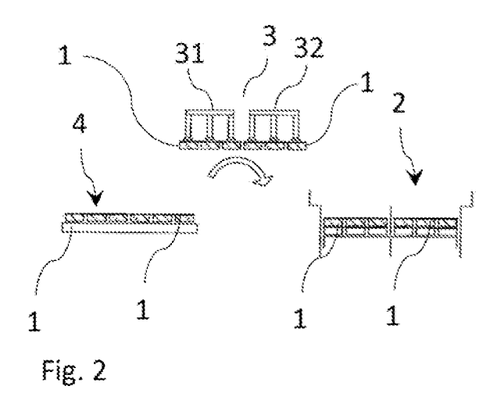
FIG. 2 shows schematically one scenario of a further exemplary embodiment of the method according to the invention using only one gripper.

FIG. 2 shows schematically the transportation of two blister strips 1 from a start location 4 directly to the autoclave magazine 2 without a hand-over station and using a first gripper 3 (which is the only gripper in FIG. 2) having two gripper units 31 and 32. Each gripper unit 31, 32 has three gripper heads in the embodiment shown (corresponding to a blister strip having three blisters). Although there is no hand-over station, the process is performed in a manner similar to the process described with the aid of FIG. 1 in which the hand-over station 5 is used.

Figure 3:
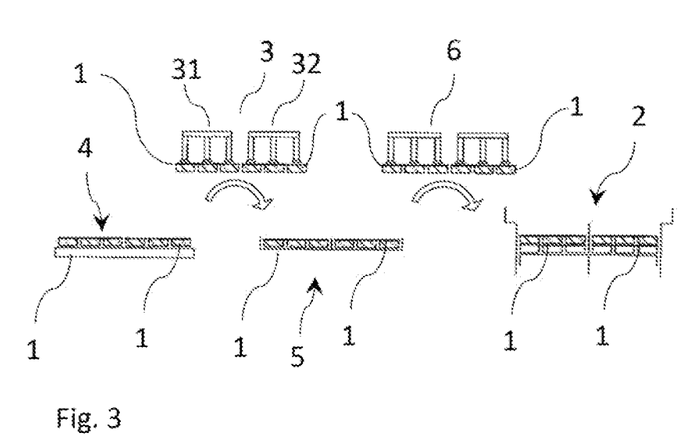
FIG. 3 shows schematically one scenario of a further exemplary embodiment of the method according to the invention using a first gripper and a second gripper.

FIG. 3 shows schematically the transportation of two blister strips 1 from the start location 4 to the hand-over station 5 (i.e. picking the two blister strips 1 up at the start location and placing them into the hand-over station 5) with the aid of the first gripper 3 having the two gripper units 31 and 32. Thereafter, the blister strips 1 are picked up at the hand-over station 5 with the aid of a second gripper 6 and are transported to the autoclave magazine 2. FIG. 3 therefore essentially corresponds to scenario A of FIG. 1.

Figure 4:
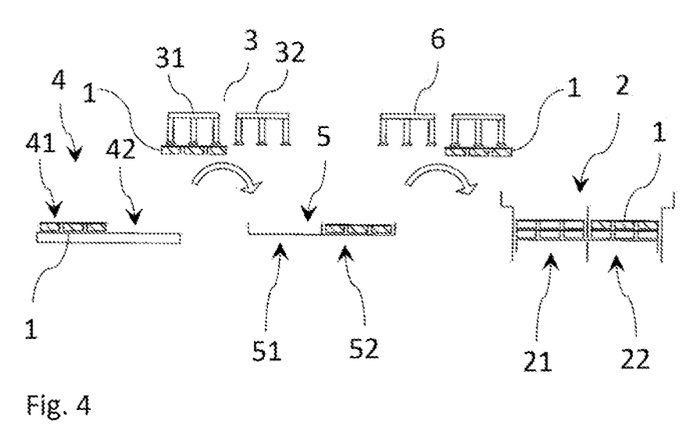
FIG. 4 shows schematically one scenario of a further exemplary embodiment of the method according to the invention using a first gripper and a second gripper with one single blister strip at the pick-up position.

FIG. 4 shows schematically the transportation of one single blister strip 1 via the hand-over station 5 to the autoclave magazine 2 in which, before transportation of the single blister strip, the second magazine compartment 22 had contained n stacked blister strips, whereas the first magazine compartment 21 had contained n+1 blister strips (non-hatched blister strips). The single blister strip 1 (hatched blister strip) is picked up at its pick-up position by the first gripper 3. In this embodiment, each gripper unit of the two gripper units 31 and 32 of the first gripper 3 is fixedly assigned to one of the two pick-up positions 41 and 42, with one gripper unit 31 being fixedly assigned to one pick-up position 41 of the two pick-up positions 41 and 42, and the other gripper unit 32 being fixedly assigned to the other pick-up position 42 of the two pick-up positions 41 and 42. However, the first gripper 3 is capable of placing the blister strip that has been picked up with either gripper unit 31 or gripper unit 32 into the hand-over station 5 at both hand-over positions 51 and 52. The second gripper 6 is configured such that it always transports a blister strip from the first hand-over position 51 of the hand-over station 5 into the first magazine compartment 21 of the autoclave magazine 2 and from the second hand-over position 52 of the hand-over station 5 into the second magazine compartment 22 of the autoclave magazine 2. Since the blister strip 1 is provided at pick-up position 41 at the start location 4 and the magazine compartment containing n blister strips in this embodiment is the second magazine compartment 22 (as opposed to the first magazine compartment 21 containing n+1 blister strips), the single blister strip 1 is picked up by gripper unit 31 and is released from gripper unit 31 at the second hand-over position 52 of the two hand-over positions 51 and 52, for the subsequent transportation of the blister strip 1 from the second hand-over position 52 to the autoclave magazine 2 and for the release of the single blister strip 1 into the second magazine compartment 22. Therefore, FIG. 4 essentially corresponds to scenario E of FIG. 1.

Figure 5:
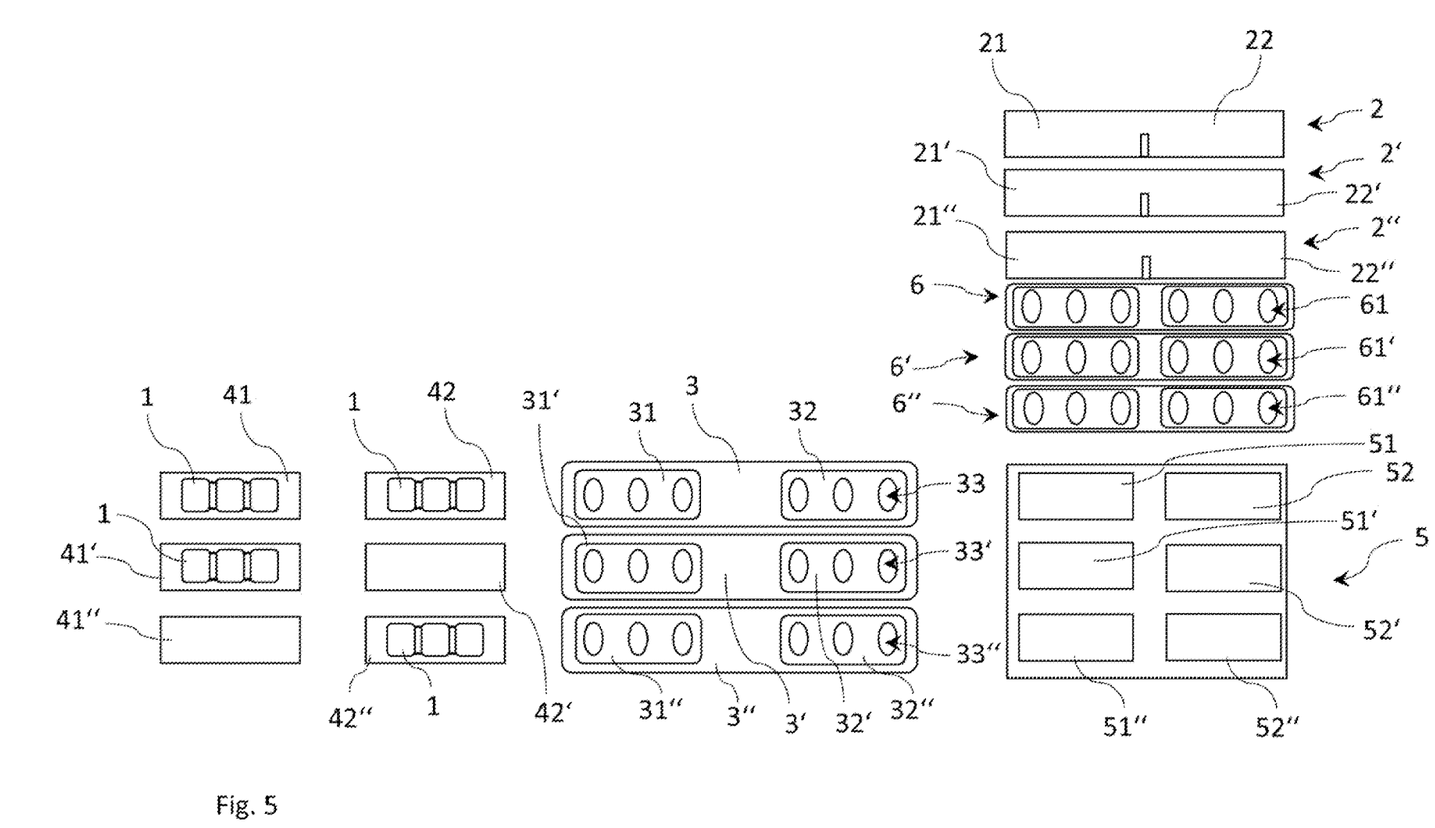
FIG. 5 shows schematically different scenarios of an exemplary embodiment of the method according to the invention with three pairs of pick-up positions in a side-by-side configuration.

FIG. 5 illustrates a further embodiment of the method for transporting blister strips 1 of ophthalmic lenses into autoclave magazines 2; 2'; 2". In this embodiment, three individual primary packaging shells are connected by a cover foil to form a three-shell blister strip 1, and three double-blister-strip transportation carriers are arranged side by side for carrying at maximum 3×2 blister strips at the pick-up positions 41, 42; 41', 42'; 41", 42".

Three first grippers 3; 3'; 3" are each equipped with two gripper units 31, 32; 31', 32'; 31", 32".

Further downstream, there is arranged a hand-over station 5 having three first hand-over positions 51; 51'; 51" and three second hand-over positions 52; 52'; 52", as well as three second grippers 6; 6'; 6" for picking the blister strips up at the hand-over station 5. These second grippers 6; 6'; 6" are completely inflexible and are only capable of picking blister strips up at the first hand-over positions 51; 51'; 51" and transporting these blister strips into the first magazine compartments 21; 21'; 21" of the autoclave magazines 2; 2'; 2", and are further only capable of picking blister strips up at the second hand-over positions 52; 52'; 52" and transporting these blister strips into the second magazine compartments 22; 22'; 22" of the autoclave magazines 2; 2'; 2".

Two three-shell blister strips 1 of the same lot are arranged on one transportation carriers during packaging, i.e. each carrier carries up to six packaging shells in total. In the embodiment shown, on the first carrier two blister strips 1 are provided at pick-up positions 41 and 42, one blister strip at each pick-up position. On the second carrier, only one single blister strip 1 is provided at pick-up position 41' whereas pick-up position 42' is empty. The third carrier provides only one single blister strip 1 at pick-up position 42" while pick-up position 41" is empty.

Each of the gripper units 31, 32; 31', 32'; 31", 32" comprises three gripping heads 33; 33'; 33" for picking up the blister strips 1 having three packaging shells. The gripping heads 33; 33'; 33" each have a bearing surface and an opening arranged in the respective bearing surface through which underpressure may be applied. The blister strips 1 are picked up at the start location 4 with the aid of the first grippers 3; 3'; 3" by positioning the gripping heads 33; 33'; 33" above the blister strips 1, by subsequently positioning the respective bearing surfaces of the gripping heads 33; 33'; 33" closely adjacent to the blister strip 1, and by applying underpressure through the opening in the respective bearing surface so as to cause the blister strips 1 to adhere to the respective bearing surface. Thereafter, the first grippers 3; 3'; 3" are moved together with the blister strips 1 adhered to the bearing surfaces to the hand-over station 5, and the blister strips 1 are then released from the bearing surface into the hand-over station 5 at the hand-over positions 51, 52; 51', 52'; 51", 52" by applying overpressure through the opening arranged in the respective bearing surface.

From the hand-over station 5, the blister strips 1 are picked up at the hand-over positions 51, 52; 51', 52'; 51", 52" with the aid of the second grippers 6; 6'; 6", each of the second grippers 6; 6'; 6" comprising three gripping heads 61; 61'; 61" for picking the blister strips 1 up. The gripping heads 61; 61'; 61" are positioned above the blister strips 1, the respective bearing surfaces of the gripping heads 61; 61'; 61" are then positioned closely adjacent to the blister strips 1, and underpressure is applied through the respective opening arranged in the respective bearing surface so as to cause the blister strips 1 to adhere to the bearing surfaces. Thereafter, the second grippers 6; 6'; 6" are moved with the blister strips 1 adhered to the bearing surfaces from the hand-over station 5 to the autoclave magazines 2; 2'; 2", where the blister strips 1 are released from the bearing surface into the corresponding magazine compartments 21, 22; 21', 22'; 21", 22" by applying overpressure through the openings in the bearing surfaces.

Figure 6:
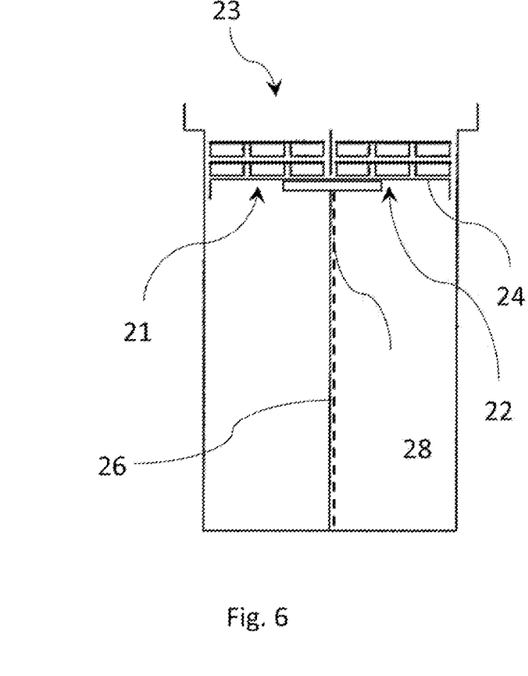
FIG. 6 shows schematically a side view of an exemplary embodiment of the autoclave magazine used in the method according to the invention.

FIG. 6 shows a side view of an embodiment of the autoclave magazine 2 that may be used in the method according to the invention. The autoclave magazine 2 comprises two internal vertically extending magazine compartments 21 and 22 which are separated from each other by a separation web 26, and further comprises a common movable compartment bottom 24 extending horizontally across both magazine compartments 21 and 22. The blister strips 1 are stacked on this common compartment bottom 24. Initially (i.e. before loading of the magazine compartments with blister strips is started), the compartment bottom 24 is arranged at the uppermost position in the vicinity of a loading opening 23 of the autoclave magazine 2. Each time one level is completely loaded with a blister strip 1 (i.e. both compartments contain the same number n of blister strips), or each time two blister strips are released into the two magazine compartments 21, 22 (i.e. one blister strip into each compartment, even if one magazine compartment may then contain n blister strips while the other magazine compartment may comprise n+1 blister strips), the compartment bottom 24 is moved downwardly to the next level (since the n-th level is completely loaded). In the embodiment shown, the compartment bottom 24 is moved up or down by a rod 28. The compartment bottom 24 rests on top of the rod 28. In the event the container bottom 24 tilts, the rod 28 may continue the downward movement during the next step, but the compartment bottom 24 may be blocked in its tilted position as it is wedged with the separation web 26. The separation web 26 thus prevents that the container bottom 24 may tilt beyond the admissible range for the operational angle of the container bottom 26 relative to the separation web 26, and thus prevents blister strips from dropping below the common compartment bottom 24 into the autoclave magazine 2 or onto the floor of the autoclave loading area.

Figure 7:
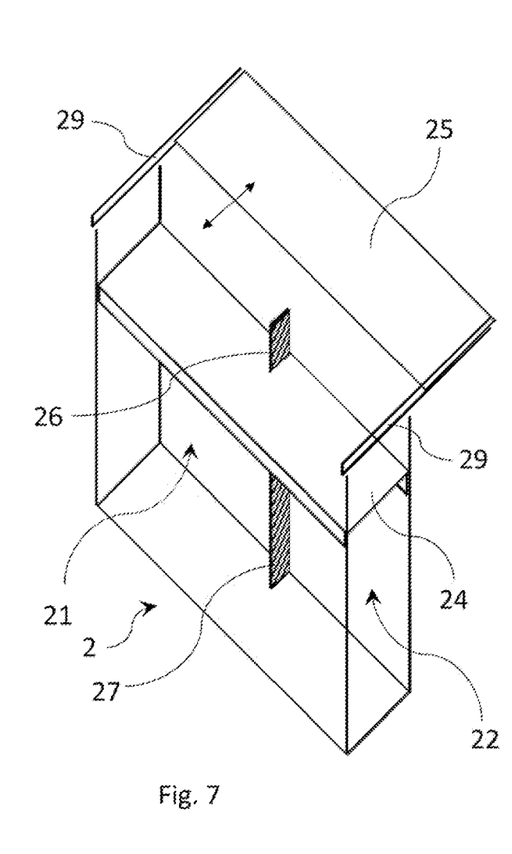
FIG. 7 shows a side elevational view of an alternative embodiment of the autoclave magazine used in the method according to the invention.

FIG. 7 shows a side elevational view of an alternative embodiment of the autoclave magazine 2. The autoclave magazine 2 comprises a separation web 26 extending along the packing axis and projecting from the rear wall of the autoclave magazine 2 into the interior space of the autoclave magazine 2. The separation web 26 separates the interior of the magazine into the two magazine compartments 21, 22. The common compartment bottom 24 comprises a slot 27 which extends from the rear end of the compartment bottom 24 in the direction towards the front end of the compartment bottom 24, for receiving the separation web 26. When the common compartment bottom 24 is moved along the packing axis, the slot 27 of the compartment bottom 24 is moved along the separation web 26.

In the embodiment shown in FIG. 7, the autoclave magazine 2 further comprises an autoclave magazine mask 25 for at least partially closing the loading opening 23. In the embodiment shown, the magazine mask 25 is designed as a magazine lid which is movable along the path indicated by the double-headed arrow (e.g. horizontally). The autoclave magazine mask 25 may for example be movable along a guide rail 29 arranged at the upper end of the magazine 2.

The autoclave magazine mask 25 has two end positions, one open position and one closed position. In the open position, the magazine mask 25 is arranged such that the entire loading opening 23 of the autoclave magazine 2 is freely accessible by the grippers transporting the blister strips, so that blister strips may be released from the grippers and placed into the magazine compartments 21, 22. In the closed position, the autoclave magazine mask 25 at least partially closes the loading opening 23 and covers at least a portion of the loading opening 23. In the closed position, the blister strips already introduced into the magazine compartments 21 and 22 of the autoclave magazine 2 may be pressed against the autoclave magazine mask 25 for compressing them by moving the compartment bottom 24 with the blister strips stacked thereon towards the autoclave magazine mask 25 until the uppermost blister strip arranged in each magazine compartment abuts against the magazine mask 25.

For example, after having introduced for example twenty blister strips into each magazine compartment, the autoclave magazine mask 25 is moved to the closed position and the common compartment bottom 24 with the blister strips arranged thereon is then moved towards the autoclave magazine mask 25 to compress the stacked blister strips contained in the magazine compartments 21, 22. After compression, the common compartment bottom 24 is moved away from the autoclave magazine mask 25 again, and the autoclave magazine mask 25 is moved to the open position to allow additional blister strips 1 to be introduced into the magazine compartments 21, 22 of the autoclave magazine 2 with the aid of the first gripper 3 or the second gripper 6 (see description above).

Figure 8:
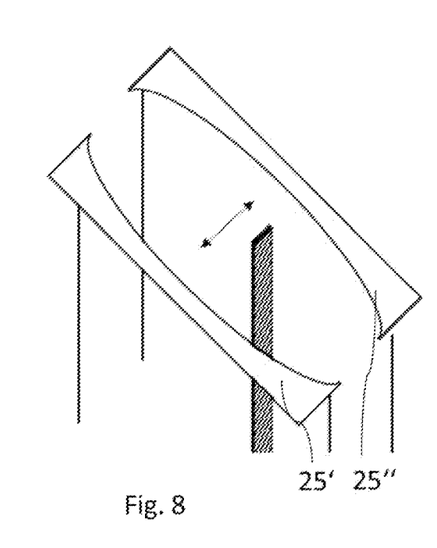
FIG. 8 shows an alternative embodiment of an autoclave magazine mask arranged at the loading opening of the autoclave magazine used in the method according to the invention.

As shown in FIG. 8, the autoclave magazine mask 25 may alternatively comprise two mask parts 25' and 25" which are movable towards and away from each other (closed and open position) along the pathway shown by the double-headed arrow in order to partially close and open the loading opening 23 of the autoclave magazine 2.

In the open position, the two mask parts 25' and 25" of the autoclave magazine mask 25 have been moved away from each other to fully expose the loading opening 23 and allow blister strips 1 to be introduced into the magazine compartments 21, 22, whereas in the closed position the two mask parts 25' and 25" of the autoclave magazine mask 25 have been moved towards each other to partially close the loading opening 23.

In addition to the advantages of the embodiment of the autoclave magazine mask 25 shown in FIG. 7, the autoclave magazine mask 25 shown in FIG. 8 may be useful for guiding the grippers during the introduction of the blister strips into the magazine compartments 21, 22, of the autoclave magazine 2.

The invention has been described with the aid of specific embodiments shown in the drawings (FIG. 1 to FIG. 8). However, for the skilled person it is evident that these embodiments have only been described by way of example, and that many changes and modifications can be made without departing from the general teaching underlying the invention. Therefore, the scope of protection is not intended to be limited to the embodiments described but rather is defined by the appended claims.

The invention claimed is:

1. Method for transporting a blister strip (1) of ophthalmic lenses, in particular contact lenses or intraocular lenses, into an autoclave magazine (2), the method comprising the steps of:
providing a first gripper (3) for gripping blister strips, the first gripper (3) comprising two gripper units (31, 32), each of the two gripper units (31, 32) being configured to separately grip one individual blister strip (1),
providing an autoclave magazine (2) comprising two magazine compartments (21, 22), each of the two magazine compartments (21, 22) being configured to contain individual blister strips (1) in a manner stacked one above the other,
at a start location (4) providing at least one blister strip (1),
picking up the at least one blister strip (1) provided at the start location (4) using the first gripper (3),
moving the first gripper (3) together with the at least one blister strip (1) picked up at the start location (4) to a destination location, and
releasing the at least one blister strip (1) from the first gripper (3) at the destination location,
wherein n is a positive integer including zero and indicates the number of blister strips actually contained in at least one of the two magazine compartments (21, 22) of the autoclave magazine (2),
wherein either the two magazine compartments (21, 22) both contain n blister strips or one magazine compartment (21, 22) contains n blister strips while the other magazine compartment (22, 21) contains n+1 blister strips,
wherein the at least one blister strip (1) is picked up at the start location (4) by the gripper units (31, 32) of the first gripper (3) and is transported to the magazine compartments (21, 22), either directly by moving the first gripper (3) to the magazine compartments (21, 22) as destination location, or indirectly by providing a hand-over station (5) and a second gripper (6) for gripping blister strips (1) and moving the first gripper (3) to the hand-over station (5) as the destination location and releasing the at least one blister strip (1) from the first gripper (3) into the hand-over station (5) and by subsequently transporting the at least one blister strip (1) from the hand-over station (5) to the magazine compartments (21, 22) using the second gripper (6),
wherein in case only one single blister strip (1) is provided at the start location (4) and one magazine compartment of the two magazine compartments (21, 22) contains n blister strips while the other magazine compartment contains n+1 blister strips,
the single blister (1) strip is picked up at the start location (4) by one of the gripper units (31, 32) of the first gripper (3) and is transported into that magazine compartment (21, 22) containing the n blister strips, either directly by moving the first gripper (3) to that magazine compartment containing the n blister strips and releasing the single blister strip (1) from the first gripper (3) into that magazine compartment, or indirectly by moving the first gripper (3) to the hand-over station (5) and releasing the single blister strip (1) from the first gripper (3) into the hand-over station (5) and subsequently transporting the single blister strip (1) from the hand-over station (5) into that magazine compartment containing the n blister strips using the second gripper (6).

2. Method according to claim 1,
wherein each gripper unit of the two gripper units (31, 32) of the first gripper (3) is either fixedly assigned to a respective magazine compartment position corresponding to the location where one magazine compartment of the two magazine compartments (21, 22) of the autoclave magazine (2) is arranged, with one gripper unit of the first gripper (3) being fixedly assigned to the magazine compartment position of one of the two magazine compartments (21, 22) and the other gripper unit of the first gripper (3) being fixedly assigned to the magazine compartment position of the other of the two magazine compartments (21, 22),
or wherein each gripper unit of the two gripper units (31, 32) of the first gripper (3) is fixedly assigned to a respective hand-over position out of two hand-over positions (51, 52) in the hand-over station (5), with one hand-over position of the two hand-over positions (51, 52) being fixedly assigned to the magazine compartment position of one of the two magazine compartments (21, 22) and the other hand-over position of the two hand-over positions (51, 52) being fixedly assigned to the magazine compartment position of the other of the two magazine compartments (21, 22),
and wherein in case only one single blister strip (1) is provided at the start location (4) and one magazine compartment of the two magazine compartments (21, 22) contains n blister strips while the other magazine compartment contains n+1 blister strips,
the single blister strip (1) is picked up at the start location (4) by that gripper unit which is fixedly assigned to the magazine compartment position corresponding to the location of the magazine compartment containing the n blister strips or to the hand-over position which is fixedly assigned to the magazine compartment position of the magazine compartment containing the n blister strips, and is transported into that magazine compartment containing the n blister strips, either directly by moving the first gripper (3) to the magazine compartment position corresponding to the location of the magazine compartment containing the n blister strips and releasing the single blister strip (1) from the first gripper into that magazine compartment, or indirectly by moving the first gripper (3) to the hand-over position fixedly assigned to the magazine compartment position of the magazine compartment containing the n blister strips and releasing the single blister strip (1) from the first gripper (3) into the hand-over station (5) at that hand-over position and by subsequently transporting the single blister strip (1) from that hand-over position in the hand-over station (5) into the magazine compartment containing the n blister strips using the second gripper (6).

3. Method according to claim 1,
wherein the start location (4) has two pick-up positions (41, 42) where blister strips (1) can be provided, and wherein each gripper unit of the two gripper units (31, 32) of the first gripper (3) is fixedly assigned to one of the two pick-up positions (41, 42), with one gripper unit being fixedly assigned to one pick-up position of the two pick-up positions (41, 42) and the other gripper unit being fixedly assigned to the other pick-up position of the two pick-up positions (41, 42),
and wherein in case only one single blister strip (1) is provided at the start location (4) at one of the two pick-up positions (41, 42) and one magazine compartment of the two magazine compartments (21, 22) contains n blister strips while the other magazine compartment contains n+1 blister strips,
the single blister strip (1) is picked up at the said one of the two pick-up positions (41, 42) by the gripper unit fixedly assigned to the said one of the two pick-up positions (41, 42) and is transported into the magazine compartment containing the n blister strips either directly by moving the first gripper (3) to the magazine compartment containing the n blister strips as the destination location and releasing the single blister strip (1) from the first gripper (3) into that magazine compartment, or indirectly by moving the first gripper (3) to the hand-over station (5) and releasing the single blister strip (1) from the first gripper (3) into the hand-over station (5) at a hand-over position fixedly assigned to the magazine compartment containing the n blister strips and by subsequently transporting the single blister strip (1) from the hand-over position into that magazine compartment using the second gripper (6).

4. Method according to claim 1,
wherein in case only one single blister strip (1) is provided at the start location (4) and both of the two magazine compartments (21, 22) contain n blister strips,
the single blister strip (1) is picked up at the start location (4) by one of the two gripper units (31, 32) of the first gripper (3), and is transported into one of the two magazine compartments (21, 22), either directly by moving the first gripper (3) to the magazine compartments (21, 22) and releasing the single blister strip (1) from the first gripper (3) into one of the two magazine compartments (21, 22), or indirectly by moving the first gripper (3) to the hand-over station (5) and releasing the single blister strip (1) from the first gripper (3) into the hand-over station (5) and by subsequently transporting the single blister strip (1) from the hand-over station (5) into one of the two magazine compartments (21, 22) using the second gripper (6).

5. Method according to claim 1,
wherein in case two blister strips (1) are provided at the start location (4) and one magazine compartment of the two magazine compartments (21, 22) contains n blister strips while the other magazine compartment contains n+1 blister strips, the two blister strips (1) are both picked up at the start location (4) by the two gripper units (31, 32) of the first gripper (3), one blister strip by one gripper unit and the other blister strip by the other gripper unit of the two gripper units (31, 32), and are transported into the two magazine compartments (21, 22), either directly by moving the first gripper (3) to the two magazine compartments (21, 22) and releasing the two blister strips (1) from the gripper units (31, 32) of the first gripper (3) into the two magazine compartments (21, 22), one blister strip into each magazine compartment, or indirectly by moving the first gripper (3) to the hand-over station (5) and releasing each of the two blister strips (1) from the first gripper (3) into the hand-over station (5), one blister strip into one hand-over position of two hand-over positions (51, 52) in the hand-over station (5) and the other blister strip into the other hand-over position of the two hand-over positions (51, 52), and by subsequently transporting the two blister strips (1) from the two hand-over positions (51, 52) in the hand-over station (5) into the two magazine compartments (21, 22), one blister into each of the two magazine compartments (21, 22), using the second gripper (6).

6. Method according to claim 1,
wherein in case two blister strips (1) are provided at the start location (4) and both of the two magazine compartments (21, 22) contain n blister strips, the two blister strips (1) are both picked up at the start location (3) by the two gripper units (31, 32) of the first gripper (3), one blister strip by one gripper unit and the other blister strip by the other gripper unit of the two gripper units (31, 32), and are transported into the two magazine compartments (21, 22), either directly by moving the first gripper (3) to the two magazine compartments (21, 22) and releasing the two blister strips (1) from the gripper units (31, 32) of the first gripper (3) into the two magazine compartments (21, 22), one blister strip into each magazine compartment, or indirectly by moving the first gripper (3) to the hand-over station (5) and releasing the two blister strips (1) from the first gripper (3) into the hand-over station (5), one blister strip into one hand-over position of two hand-over positions (51, 52) in the hand-over station (5) and the other blister strip into the other hand-over position of the two hand-over positions (51, 52), and by subsequently transporting the two blister strips (1) from the two hand-over positions (51, 52) in the hand-over station (5) into the two magazine compartments (21, 22), one blister strip into each of the two magazine compartments (21, 22), using the second gripper (6).

7. Method according to claim 1,
wherein providing an autoclave magazine (2) comprises providing an autoclave magazine (2) having a packing axis, the two magazine compartments (21, 22), a loading opening (23) and a common compartment bottom (24) arranged normal to and movable along the packing axis, and
wherein, prior to releasing blister strips (1) into the two magazine compartments (21, 22) of the autoclave magazine (2), the compartment bottom (24) is moved to an uppermost position at the loading opening (23), and only then the blister strips (1) are transported to and released into the magazine compartments (21, 22), and
wherein each time either two blister strips are released into the two magazine compartments (21, 22), one blister strip into one of the two magazine compartments and the other blister strip into the other magazine compartment of the two magazine compartments or
each time only one single blister strip is released into one of the magazine compartments, when both of the two magazine compartments (21, 22) contain the same number m of blister strips, with m being a positive integer excluding zero and being less than a maximum number of blister strips to be accommodated in each of the magazine compartments (21, 22), the compartment bottom (24) is moved away from the loading opening (23) along the packing axis by one step to allow for additional blister strip(s) (1) to be released into the magazine compartments (21, 22).

8. Method according to claim 7, wherein the method comprises providing an autoclave magazine mask (25) arranged at the loading opening (23) of the autoclave magazine (2), the autoclave magazine mask (25) being capable of being opened and closed and, after having released into the two magazine compartments a predefined number of blister strips which is less than the maximum number of blister strips to be accommodated in the two magazine compartments (21, 22), the autoclave magazine mask (25) is closed, the compartment bottom (24) is then moved towards the autoclave magazine mask (25) to compress the stacked blister strips contained in the magazine compartments (21, 22), and the autoclave magazine mask (25) is then opened again to allow for additional blister strips to be released from the first gripper (3) or the second gripper (6) into the magazine compartments (21, 22) of the autoclave magazine (2), wherein the closed autoclave magazine mask (25) covers at least a portion of the loading opening (23) for allowing a respective uppermost blister strip of the stacked blister strips accommodated in the magazine compartments to abut against the autoclave magazine mask (25) as the compartment bottom (24) is moved towards the autoclave magazine mask (25).

9. Method according to claim 8, wherein after the compartment bottom (24) has been moved towards the autoclave magazine mask (25) to compress the stacked blister strips contained in the magazine compartments (21, 22), the compartment bottom (24) is moved away from the autoclave magazine mask (25) again, and the autoclave magazine mask (25) is opened to allow additional blister strips (1) to be released into the magazine compartments (21, 22) of the autoclave magazine (2) with the aid of the first gripper (3) or the second gripper (6).

10. Method according to claim 8, wherein providing an autoclave magazine (2) comprises providing an autoclave magazine (2) comprising a separation web (26) extending along the packing axis, the separation web (26) separating the interior of the magazine into the two magazine compartments (21, 22), and wherein the compartment bottom (24) comprises a slot (27) for receiving the separation web (26), and wherein moving the compartment bottom (24) along the packing axis comprises moving the slot (27) of the compartment bottom (24) along the separation web (26).

11. Method according to claim 1, wherein transporting the blister strips (1) using the first gripper (3) or the second gripper (6) comprises the steps of providing the first gripper (3) or the second gripper (6) with gripping heads (33, 61), the gripping heads (33, 61) each having a bearing surface and at least one opening in the respective bearing surface, picking the blister strip(s) (1) up with the first gripper (3) or the second gripper (6) by positioning the gripping heads (33, 61) of the first gripper (3) or the second gripper (6) above the blister strip(s) (1), by placing the respective bearing surfaces closely adjacent to the blister strip (1), and by applying underpressure through the opening in the respective bearing surface so as to cause the blister strip(s) (1) to adhere to the respective bearing surface, moving the first gripper (3) or the second gripper (6) together with the blister strip(s) (1) adhered to the bearing surface to a desired location, and releasing the blister strip(s) (1) from the bearing surface at the desired location by applying overpressure through the opening in the respective bearing surface.

12. Method according to claim 11, wherein the method comprises providing a first gripper (3) or second gripper (6) further having a detection opening in the respective bearing surface, and applying a separate underpressure through the detection opening in the respective bearing surface in order to detect whether or not a blister strip (1) is adhered to the respective bearing surface.

* * * * *